United States Patent [19]

Okada

[11] Patent Number: 4,887,997

[45] Date of Patent: Dec. 19, 1989

[54] CATHETER FOR NASOGASTRIC INTUBATION

[75] Inventor: Yosuke Okada, Mori, Japan

[73] Assignee: Sherwood Medical Company, St. Louis, Mo.

[21] Appl. No.: 244,557

[22] Filed: Sep. 12, 1988

Related U.S. Application Data

[63] Continuation of Ser. No. 933,642, Nov. 21, 1986, abandoned.

[51] Int. Cl.$^4$ ............................................. A61M 25/00
[52] U.S. Cl. ...................................... 604/54; 604/161; 604/164; 604/280; 604/171
[58] Field of Search ...................... 604/53, 54, 158–172, 604/280

[56] References Cited

U.S. PATENT DOCUMENTS

| | | | |
|---|---|---|---|
| 3,459,184 | 8/1969 | Ring | 604/164 |
| 4,099,528 | 7/1978 | Sorenson et al. | 604/164 X |
| 4,175,564 | 11/1979 | Kwak | 128/350 R |
| 4,291,694 | 9/1981 | Chai | 605/53 X |
| 4,326,520 | 4/1982 | Alley | 604/171 |
| 4,402,685 | 9/1983 | Buhler et al. | 604/280 |
| 4,581,019 | 4/1986 | Curelaru et al. | 604/164 |
| 4,631,059 | 12/1986 | Wolvek et al. | 604/164 X |
| 4,687,470 | 8/1987 | Okada | 604/171 |

Primary Examiner—Dalton L. Truluck
Attorney, Agent, or Firm—Andrew J. Beck; Montgomery W. Smith; Richard D. Allison

[57] ABSTRACT

This invention provides a catheter for nasogastric intubation comprises a tube for nasogastric intubation and a plastic separator, said tube for nasogastric intubation consisting of a catheter and a plastic sheath tube having a longitudinal tear-off line over full length thereof together with elasticity and rigidity slightly larger than those of said catheter inserted slidably thereinto, and said separator for splitting said sheath tube fixing said tube at the vicinity of a nostril.

14 Claims, 3 Drawing Sheets

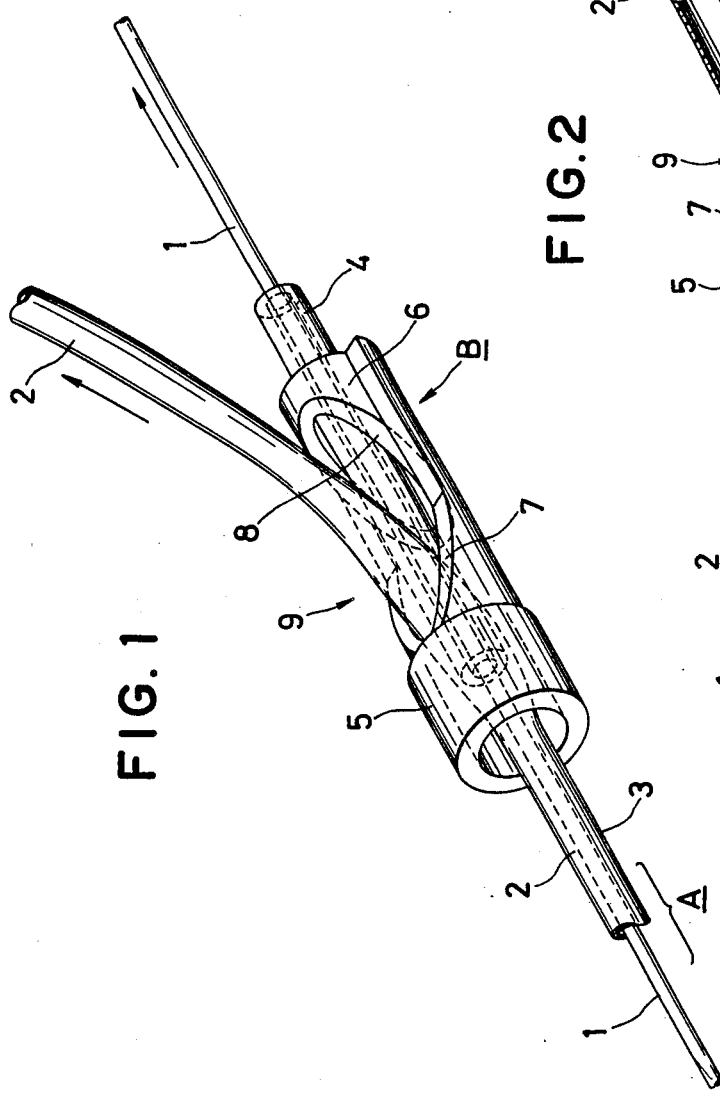
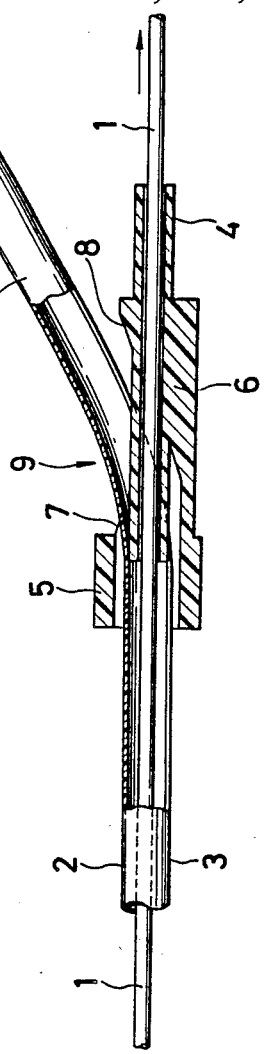
FIG.1
FIG.2

CATHETER FOR NASOGASTRIC INTUBATION

This is a continuation of co-pending application Ser. No. 933,642 filed on Nov. 21, 1986, now abandoned.

BACKGROUND OF THE INVENTION

1. Field of the Invention

The present invention relates to a catheter for nasogastric intubation.

2. Description of the Prior Art

Normally, a catheter for nasogastric intubation to be used for nutritional purposes comprises a weighted portion in which a weight is sealed into a distal end of a soft small-diameter plastic tube. The weighted portion is inserted through nostril into the esophagus and into the stomach or the intestines the weight facilitating catheter placement for supply of a nutritious liquid through one or two side holes positioned slightly above the weighted portion.

Since the catheter remains positioned in and through the nostril for a long period of time, a patient may feel considerable pain. To avoid such pain, the catheter is preferably formed of a material as soft as possible. Moreover, since the catheter remains in contact with the walls of the internal organs for a long period of time, if the catheter is formed of a hard material, the tissue of the walls of the internal organs may be injured.

Also, for this reason, it is desired that the catheter be formed from a soft plastic tube. However, and such tube has to be inserted into the stomach and intestines following a torvous path nostril, through the the narrow-passage larynx and the esophagus and therefor a catheter made of a soft plastic tube lacks the requisite stiffness and is difficult to insert.

In the past, therefore, a method has been employed in which a guide wire is inserted into the boil of the catheter to increase the catheter stiffness. In this proposal, however, insertion of the guide wire into the catheter a lubricant be used to coat the internal surfaces of the bore of the catheter to decrease the frictional resistance therebetween. Such procedure is unnecessarily time consuming, and in addition, insertion of the guide wire is cumbersome. Furthermore, such procedure may result in profiction the end of the guide wire through one of the side holes of the catheter where it may pierce the walls of the internal organs.

SUMMARY OF THE INVENTION

This invention overcomes the disadvantages noted above. According to the present invention, a catheter is inserted and encased into a plastic insertion guide or sheath tube having a longitudinal tear-off line over the full length and there of having elasticity and rigidity slightly greater than those of the catheter. The catheter and encasing sheath tube are inserted together through the patient's nostril, larynx and esophagus into the stomach or intestines. A separator positioned just outside the nostril splits the sheath tube and holds the catheter as the sheath tube is withdrawn from around the intubated catheter. The separator includes an inner tube projecting into the bore of an outer tube of the separator. The catheter extends within and through the inner tube, and the separator is positioned along the catheter near the nostril. The sheath tube is extended over the end, and around the outside of, the inner tube, and is then split along the tear-off line as the sheath tube is pulled from around the inner tube and out through an opening in the side of the outer tube of the separator.

BRIEF DESCRIPTION OF THE DRAWINGS

FIG. 1 is a perspective view of the catheter, sheath tube and separator according to this invention, showing the position of the sheath and catheter in the separator during sheath withdrawal.

FIG. 2 is an axial section view of the catheter, sheath tube and separator shown in FIG. 1.

DETAILED DESCRIPTION OF THE INVENTION

Figure 3:
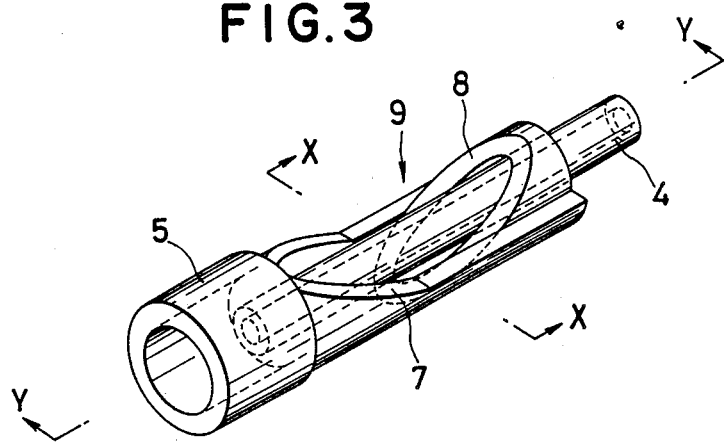
FIG. 3 is a perspective view of the spearator.

Referring to FIG. 1, catheter 1 is made of a soft plastic. As described above, sheath tube 2 is a plastic tube having elasticity and rigidity slightly greater than those of the catheter, and is preferably provided with a longitudinal tar-off line 3 over substantially the full length of the sheath tube. The tear-off line 3 is preferably formed by integrating a line material dissimilar to and weaker than the material of which the sheath tube 2 is made, longitudinally along one side of the sheath tube. Alternatively, the tear-off line 3 may be formed by decreasing the wall thickness of the sheath tube 2 longitudinally along one side of the sheath tube 2. It will be understood that although only a single tear-off lines is shown in the drawings, there may be more than one such longitudinal tear-off line. However, it is desirable that the tear-off line does not extend through a very small area 10 at the distal end of the catheter.

A separator for holding the catheter is made of slightly hard plastics, and is set near the nostril. The separator includes an inner tube 4 having an inner bore of the separator sufficient in diameter to slidably receive the catheter 1 therein, and an outer tube 5 having a bore of sufficient diameter to slidably accept the sheath tube therein. The outer tube 5 is positioned coaxially with the inner tube 4, the bore of the outer tube being sufficient to form an annulus between the outside surface of the inner tube and the bore of the outer tube 5. The separator is provided with a closed portion 6 which occludes a portion of the annulus between both tubes 4 and 5. The bore of the inner tube 4 extends through the closed portion 6 to a back end of the inner tube 4, while a front end of the inner tube extends within the bore of the outer tube toward, but not to, an open end of the outer tube 5. Further, a portion of the outer tube 5 is cut out to form a side opening 9 positioned longitudinally between the closed portion 6 and the front end of the inner tube 4. As shown in the drawings, the closed portion 6 has an axially or longitudinally inclining face 8, and the side opening 9 in the outer tube 5 has an oppositely inclined face portion 7 opposite the closed portion 6 and inclining face 8.

Although for ease of removal of the sheath tube 2 the tear-off line 3 is disclosed herein as being formed in the sheath tube prior to use and withdrawal of the sheath tube 2 after intubation, it is also possible with the present invention to use a sheath tube 2 having no tear-off line 3, that is withdrawn from around the catheter by longitudinally splitting one side of the sheath tube 2 with a cutter (not shown), mounted or formed in the separator near the inner tubes opposite the side opening as the sheath tube 2 is pulled out through the side opening 9 of the separator.

The separator is installed on the catheter 4 and sheath tube 2 by inserting the catheter 1 into the inner tube 4 while slightly splitting the sheath tube and positioning the split end of the sheath tube 2 within the annulus between the tubes 4 and 5. The sheath tube 2 is then pulled through the opening 9 in the tube 5, and while catheter 1 is pulled through the inner tube 4, in directions shown by the arrows in FIGS. 1 and 2. Once the separator is positioned near the nostril and the catheter 1 is satisfactorily emplaced, the sheath tube 2 is continuously drawn out upward from the side opening 9, splitting the tube 2 at eh tear-off line 3 responsive to pullin the sheath tube 2 against the inner tube 4 until the sheath tube 2 is entirely drawn out, thereby leaving the catheter 1 intubated in the stomach and the intestines.

Figure 4:
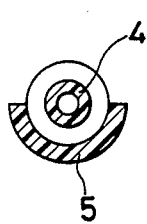
FIG. 4 is a section view taken along line X—X of FIG. 3.
Figure 5:
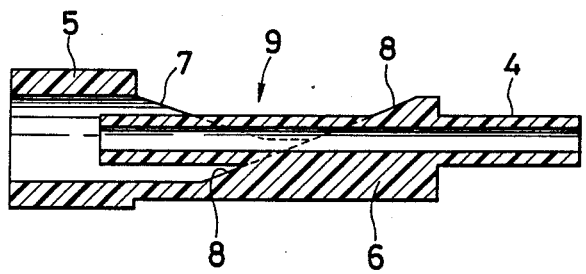
FIG. 5 is a section view of the separator taken along line Y—Y of FIG. 3.

The features of the separator shown in FIGS. 1 and 2 and described above may also be seen in FIGS. 3, 4 and 5, showing the separator without the catheter 1 and sheath tube 2. The separator closed protion 6, outer tube 5, and inner tube combine to form the body of the separator.

Figure 6:
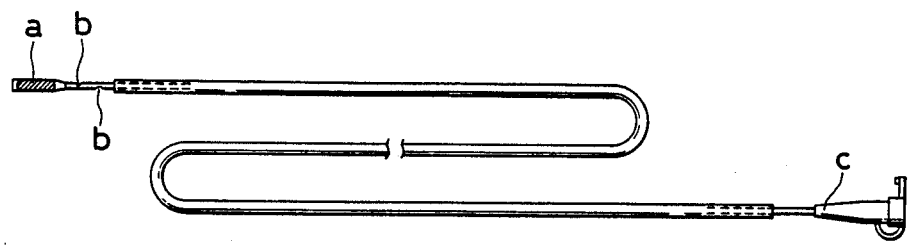
FIG. 6 is a plan view of the catheter and sheath tube without the separator.
Figure 7:
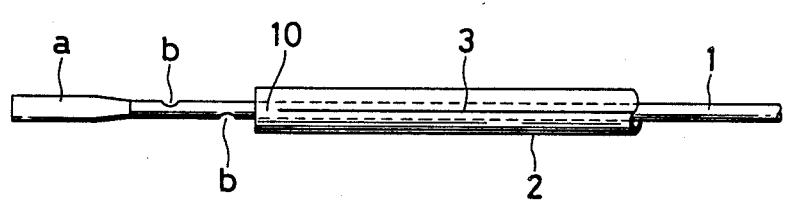
FIG. 7 is an enlarged plan view of the distal end of the catheter and sheath tube shown in FIG. 6.

The catheter 1 is shown in FIG. 6, wherein the letter A designates a weight portion at a distal end of the catheter 1, the letter B designates side holes from which a nutritous liquid is supplied into the stomach or intestines from the distal end of the catheter 1, and the letter C designates a securing portion at a proximal end of the catheter 1 for connecting the catheter to a bottle of nutritional liquid. The enlarged view of the distal end of the catheter 1 shown in FIG. 7 clearly shows sheath tube 2, the tear-off line of the sheath tube 2, and the non-tearing portion 10 thereof.

Figure 8:
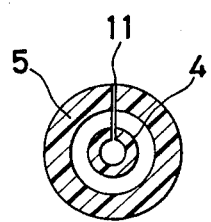
FIG. 8 is a section view of a second embodiment of the separator taken along substantially the same lines as the section view of FIG. 4.

FIG. 8 shows a second example of a separator according to this invention, wherein an axially extending slit 11 is provided through the outer tube 5, the closed portion 6, and the inner tube 4, to the center or axis of the separator.

Figure 9:
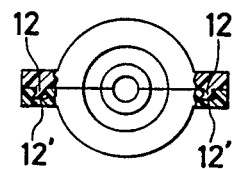
FIG. 9 is a section view of a third embodiment of the separator taken along substantially the same lines as the section view of FIG. 4.

A third embodiment of a separator according to this invention is shown in FIG. 9, wherein the separator is longitudinally divided into two parts. Inserting projections 12 and inserted holes 12', adapt the two parts of the separator to be removably integrated to each other. The separator is installed on the catheter 1/sheath tube 2 combination by separating the two parts, and then integrating the parts to form the separator with the catheter 1 and sheath tube 2 appropriately positioned therein.

In the operation of this invention, the catheter 1 is encased in the sheath tube 2, and the combination is inserted into the interal organs as mentioned above. After intubation, the sheath tube 2 can be smoothly and easily drawn up from the interal organs by splitting the sheath tube 2 with the inner tube, or splitting means on the separator for splitting the sheath tube 2 responsive to withdrawal of the sheath tube from around the inner tube 4.

Further by setting this separator at the nostril, the operation can be performed by a single person as compared with two persons in a conventional method. Since the sheath tube has slightly greater elasticity and rigidity than that of the catheter, the insertion into the stomach and the intestines thereof can be performed very easily and rapidly. Since the drawn out sheath tube can be performed smoothly and promptly, a patient feels minimal discomfort. The sheath tube and the separator can be produced at low cost because they can be easily formed out of plastic.

What is claimed is:

1. A medical intubation assembly, a distal end of which is adapted to be inserted internally of a patient, said assembly comprising
    a catheter having distal and proximal ends and a length sufficient to reach from externally of a patient to a desired point internally of the patient;
    a longitudinally splittable sheath tube having slightly greater rigidity than said catheter and having an internal bore slidably receiving and encasing said catheter; and
    a separator having distal and proximal ends that is mountable on the proximal end of said catheter at the vicinity of the nostril for longitudinally separating the sheath tube from said catheter said separator including a rigid inner tube having a bore extending through said separator, the bore of the inner tube being adapted to receive the catheter therethrough and to receive the sheath tube therearound, said separator also including a closed portion longitudinally positioned along the inner tube for occluding a space around the inner tube and for longitudinally separating the sheath tube from the catheter responsive to withdrawal of the sheath tube from around the inner tube.

2. The assembly of claim 1, wherein said separator includes an outer tube on the distal end thereof and positioned about said inner tube to form an annular space between the inner tube and the outer tube, said outer tube having a side opening therein positioned such that the sheath tube may be withdrawn through said side opening from around said inner tube.

3. The assembly of claim 2, wherein said closed portion defines a first side of said side opening.

4. The assembly of claim 3, wherein the closed portion defining said first side opening is longitudinally inclined.

5. The assembly of claim 3, wherein said sheath tube has a longitudinal tear-off line therealong substantially the full length of the sheath tube and said sheath tube is separated from the catheter by contacting the outside surface of said inner tube and said closed portion of said separator.

6. The assembly of claim 8, wherein said tear-off line is formed by a longitudinal, linear weakened portion of the sheath tube.

7. The assembly of claim 1, wherein the catheter includes a weighted section and a plurality of openings on the distal end thereof.

8. An assembly for facilitating the withdrawal of a sheath tube from an encasing and slidable position about a catheter, said catheter having distal and proximal ends and a length sufficient to reach from externally of a patient to a desired point internally of a patient, said assembly comprising a catheter having distal and proximal ends and wherein said catheter is slidably received in and substantially enclosed in a longitudinally splittable sheath tube, a separator body having distal and proximal ends and a bore extending therethrough adapted to receive said catheter, a portion of said bore being formed by an inner tube of said body adapted to slidably receive said sheath tube therearound at the distal end of said body, and a separating means for longitudinally separating said sheath tube from said catheter responsive to withdrawal of the sheath tube from around said inner tube while said catheter is fixed within said inner bore.

9. The separator of claim 8, wherein said body further includes an outer tube extending around a portion of said inner tube on the distal end of said body, said outer tube and inner tube forming an annular space therebetween within which said sheath tube extends about the inner tube, said body further including a closed portion about said inner tube occluding said annular space, and said distal end of said body having a side opening proximal to the outer tube and therein through which said sheath tube may be withdrawn from said inner tube.

10. The separator of claim 9 wherein said closed portion has a longitudinally inclined face defining a first side portion of said side opening spaced apart from said annular space.

11. A separator for facilitating the withdrawal of a sheath tube from an encasing and slidable position about a catheter, said catheter having distal and proximal ends and a length sufficient to reach from externally of a patient to a desired point internally of a patient, said separator comprising a separator body having distal and proximal ends and a bore extending therethrough adapted to receive said catheter, a portion of said bore being formed by an inner tube of said body adapted to slidably receive said sheath tube therearound at the distal end of said body.

a separating means for longitudinally separating said sheath tube from said catheter responsive to withdrawal of the sheath tube from around said inner tube while said catheter is fixed within said inner bore, and wherein the body includes an outer tube on the distal end thereof, a closed portion within said outer tube, said inner tube being positioned within said closed portion and extending from the proximal end of said body to a position near the distal end of said body and extending through and past said closed portion, a side opening having first and second sides in said outer tube wherein said side opening on said outer tube includes an inclined second side opposite the closed portion of said outer tube, and said side opening of said outer tube having an inclined first side adjacent to said closed portion of said outer tube.

12. The separator of claim 11, wherein the closed portion is inclined within the annular space between the outer and inner tubes.

13. An assembly for facilitating the withdrawal of a sheath tube from an encasing and slidable position about a catheter, said catheter having a length to reach from externally of a patient to a desired point internally of a patient, said assembly comprising a longitudinally splittable sheath substantially enclosing a catheter slidably received therein, a separator body having a bore extending therethrough adapted to receive said catheter, a portion of said bore being formed by an inner tube of said body adapted to slidably receive said sheath tube therearound, said inner tube being rigid and providing means for longitudinally separating the sheath tube from the catheter responsive to longitudinal withdrawal of the sheath tube from around the inner tube.

14. A method for inserting a nasal gastric tube into a patient, comprising the steps of:

inserting an elongate catheter having distal and proximal ends and a sheath tube encasing and slidably positioned about said catheter into the nasal gastric passage of a patient, attaching a separator to the proximal end of the catheter wherein the separator includes distal and proximal ends and an inner bore formed by an inner tube extending from the proximal end of said separator to a spaced relation with an outer tube on the distal end of said separator, removing the tubular sheath from the nasal gastric passage of the patient by manually placing the catheter and tubular sheath into the separator wherein the catheter is enclosed within the inner tube of the separator and the tubular sheath encircles a portion of the inner tube in a passageway formed between the inner tube and the outer tube, separating the tubular sheath from the catheter by moving the tubular sheath through the passageway formed between the inner tube and outer tube until the tubular sheath contacts a closed end portion of the outer tube having a side opening adjacent thereto wherein further movement of the tubular sheath causes the closed end portion of the outer tube to separate the tubular sheath from the contacting relation with inner tube and pass outwardly from the separator through the side opening.

* * * * *